United States Patent [19]

Lauer et al.

[11] Patent Number: 5,134,167

[45] Date of Patent: Jul. 28, 1992

[54] 1-AZABUTADIENES AND FUNGICIDES CONTAINING THESE COMPOUNDS

[75] Inventors: Manfred Lauer, Ludwigshafen; Bernhard Zipperer, Dirmstein; Norbert Goetz, Worms; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 551,174

[22] Filed: Jul. 11, 1990

[30] Foreign Application Priority Data

Jul. 19, 1989 [DE] Fed. Rep. of Germany ....... 3923896

[51] Int. Cl.$^5$ ................. A61K 31/15; C07C 251/32
[52] U.S. Cl. ................. 514/640; 514/590; 514/639; 514/641; 514/357; 546/330; 546/329; 546/340; 546/339; 564/36; 564/251; 564/253; 564/254; 564/271; 564/277; 568/425; 568/448
[58] Field of Search ............ 564/254, 255, 253, 36, 564/251, 271, 277, 256; 514/640, 521, 520, 519, 590, 639, 641; 560/168; 546/330

[56] References Cited

U.S. PATENT DOCUMENTS 1,834,850 12/1931 Kropp .................. 564/277
3,903,303 9/1975 Gutman .................. 514/640
3,992,538 11/1976 Teufel et al. .................. 564/254
4,061,772 12/1977 Teufel et al. .................. 424/304
4,383,948 5/1983 Müller et al. .................. 564/251
4,467,120 8/1984 Fischer et al. .................. 568/484
4,767,768 8/1988 Okamoto et al. .................. 514/315

*Primary Examiner*—Glennon H. Hollrah
*Assistant Examiner*—Shailendra Kumar
*Attorney, Agent, or Firm*—Oblon, Spivak, McClelland, Maier & Neustadt

[57] ABSTRACT

1-Azabutadienes of the formula

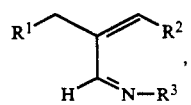

where $R^1$ and $R^2$ are each phenyl, biphenyl, naphthyl or pyridyl, and these radicals may be substituted, or are each alkyl which is unsubstituted or substituted, $R^3$ is substituted or unsubstituted phenyl or a radical $OR^4$, where $R^4$ is hydrogen, alkyl or an aromatic or aliphatic acyl group, or $R^3$ is a radical $NHR^5$, where $R^5$ is hydrogen, substituted or unsubstituted phenyl, or the carbamide group, and fungicidal agents containing these compounds.

8 Claims, No Drawings

1-AZABUTADIENES AND FUNGICIDES CONTAINING THESE COMPOUNDS

The present invention relates to 1-azabutadienes and fungicides containing these compounds.

We have found novel 1-azabutadienes of the formula I

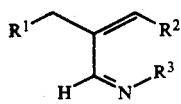

where
$R^1$ and $R^2$ are identical or different and are each phenyl, biphenyl, naphthyl or pyridyl, and these radicals may be monosubstituted to trisubstituted by halogen, nitro, phenoxy, amino, haloalkyl, alkyl or alkoxy, each of 1 to 4 carbon atoms, or are each straight-chain or branched $C_1$-$C_8$-alkyl which is unsubstituted or substituted by unsubstituted or substituted phenyl, and
$R^3$ is unsubstituted or substituted phenyl or a radical $OR^4$, where
$R^4$ is hydrogen, straight-chain or branched $C_1$-$C_6$-alkyl or an aromatic or aliphatic acyl group, or $R^3$ is a radical $NHR^5$, where
$R^5$ is hydrogen, unsubstituted or substituted phenyl or the carbamide group $CONH_2$, which have a very good fungicidal action.

In formula I, $R^1$ and $R^2$ independently of one another are each, for example, 1-naphthyl, 2-naphthyl, 2-pyridyl, 3-pyridyl, 4-pyridyl, p-biphenyl, phenyl, halophenyl, e.g. 2-fluorophenyl, 3-fluorophenyl, 4-fluorophenyl, 2-chlorophenyl, 3-chlorophenyl, 4-chlorophenyl, 2-bromophenyl, 3-bromophenyl or 4-bromophenyl, halo-$C_1$-$C_4$-alkylphenyl, e.g. 2-trifluoromethylphenyl, 3-trifluoromethyllphenyl or 4-trifluoromethylphenyl, $C_1$-$C_4$-alkylphenyl, or 2-methylphenyl, 3-methylphenyl or 4-methylphenyl, $C_1$-$C_4$-alkoxyphenyl, e.g. 2-methoxyphenyl, 3-methoxyphenyl or 4-methoxyphenyl, 2,3-dichlorophenyl, 2,4-dichlorophenyl, 2,5-dichlorophenyl, 2,6-dichlorophenyl, 2-chloro-6-fluorophenyl, 2-chloro-4-fluorophenyl, 2-fluoro-4-chlorophenyl, 2,4-dimethylphenyl, 2,6-dimethylphenyl or 2,4,6-trimethylphenyl or $C_1$-$C_8$-alkyl, in particular $C_1$-$C_4$-alkyl, e.g. methyl, ethyl, propyl, isopropyl, butyl, sec-butyl, tert-butyl, pentyl or 2,2-dimethylpropyl, benzyl, halobenzyl, e.g. 4-chlorobenzyl or 4-fluorobenzyl, $C_1$-$C_4$-alkylbenzyl, e.g. 4-methylbenzyl, 2-chlorobenzyl, 2-fluorobenzyl, 2-methylbenzyl or 2-phenylethyl, halophenylethyl, e.g. 4-chlorophenylethyl or 4-fluorophenylethyl, or 3-phenylpropyl.

Particularly preferred compounds are those in which $R^1$ is an unsubstituted or substituted phenyl ring, for example phenyl or halophenyl, e.g. 4-chlorophenyl, 4-fluorophenyl, 2-chlorophenyl or 2-fluorophenyl, and $R^2$ is 2,2-dimethylpropyl or 3,3-dimethylbutyl or unsubstituted or substituted phenyl, for example phenyl or halophenyl, e.g. 4-chlorophenyl, 4-fluorophenyl, 2-chlorophenyl or 2-fluorophenyl.

$R^3$ is, for example, hydroxyl or the group $OR^4$, where $R^4$ is an aliphatic or aromatic acyl radical, for example $C_1$-$C_4$-alkyl-CO, acetyl, propionyl, butyryl, benzoyl or halobenzoyl, e.g. 4-chlorobenzoyl, or unsubstituted or substituted $C_1C_6$-alkyl, in particular $C_1$-$C_4$-alkyl, such as methyl, ethyl, propyl or butyl, benzyl or halobenzyl, or $R^3$ is a radical $NHR^5$, where $R^5$ is hydrogen, the carbamide group $CONH_2$ or unsubstituted or substituted phenyl, for example phenyl or nitrophenyl, e.g. 4-nitrophenyl or 2,4-dinitrophenyl.

Finally, $R^3$ is furthermore unsubstituted or substituted phenyl, for example phenyl, halophenyl, such as 4-chlorophenyl or 4-bromophenyl, or $C_1C_4$-alkylphenyl, such as 4-methylphenyl.

$R^3$ is particularly preferably hydroxyl and derivatives derived therefrom which can be obtained by alkylation or acylation.

1-Azabutadienes of the formula I can be obtained, for example, by reacting an aldehyde II

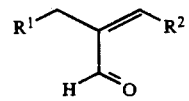

with a compound of the formula $H_2N$-$R^3$ in the presence or absence of a catalyst and of a suitable solvent. Waterremoving agents, such as molecular sieves, such as magnesium sulfate, sodium sulfate or calcium chloride, may be used as catalysts, as well as acids, such as sulfuric acid, hydrochloric acid or acetic acid, or basic compounds, such as sodium hydroxide, potassium hydroxide, potassium carbonate or potassium acetate. Examples of solvents are lower alcohols, such as methyl alcohol or ethyl alcohol, and their mixtures with water, as well as propyl alcohol, isopropyl alcohol, butanol, sec-butanol or tert-butanol, ketones, such as acetone, ethers, such as diethyl ether, tetrahydrofuran or methyl tert-butyl ether, and methylene chloride, aromatic hydrocarbons, such as toluene or xylene, and dimethylformamide and dimethyl sulfoxide.

Method 1

5,5-Dimethyl-2-formyl-1-(p-chlorophenyl)-hex-2-ene (compound 136a)

79 g (0.79 mol) of 3,3-dimethylbutyraldehyde are added to a solution of 10.5 g of 50% strength by weight aqueous NaOH in 500 ml of methanol, after which 123 g (0.73 mol) of p-chlorodihydrocinnamaldehyde are added dropwise at 34° C. The mixture is stirred for one hour and then neutralized with dilute sulfuric acid, the solution is evaporated down and the residue is then subjected to fractional distillation.

Bp. 119°-122° C/0.01 mbar, yield 115.9 g (59% of theory)

Method 2

1-(o-Chlorophenyl)-3-(p-fluorophenyl)-2-formyl-prop-1-ene 71.7 g (0.51 mol) of 2-chlorobenzaldehyde are added to a solution of 4 g of 50% strength sodium hydroxide solution in 300 ml of methanol while cooling, at a rate such that the temperature does not exceed 20° C. 70.0 g (0.46 mol) of p-fluorodihydrocinnamaldehyde are then added dropwise at 25°-30° C. in the course of 4 hours. Stirring is continued for one hour at 30° C., the mixture is neutralized with dilute sulfuric acid and evaporated down and the residue is distilled.

Bp. 164°-184° C./0.3 mbar; yield 97.8 g (77% of theory)

Method 3

4,4-Dimethyl-2-formyl-1-(p-chlorophenyl)-pent-1-ene (compound 63a)

134 g (0.95 mol) of 4-chlorobenzaldehyde are added to a solution of 15.8 g of 50% strength sodium hydroxide solution in 500 ml of methanol, after which 90 g (0.79 mol) of 4,4-dimethylpentanal are added dropwise at 35° C. in the course of 3 hours. Stirring is carried out for three hours, after which the mixture is neutralized with dilute sulfuric acid and evaporated down and the residue is distilled.

Bp. 117°–120° C./0.4 mbar; yield 83.5 g (39% of theory)

PREPARATION EXAMPLE 1 compound 136

4.2 g (0.06 mol) of hydroxylammonium hydrochloride, dissolved in a methanol/water mixture, and 4.1 g (0.03 mol) of potassium carbonate were added to a solution of 7.5 g (0.03 mol) of the aldehyde from method 1 in 100 ml of methanol. After a reaction time of one hour at 25° C., the mixture was evaporated down and the product was extracted with methylene chloride. Yield 6.8 g (85% of theory), mp. 78° C.

PREPARATION EXAMPLE 2 compound 139

5.0 g (0.019 mol) of the oxime from Example 1 were dissolved in 50 ml of tetrahydrofuran, and 3.0 g of pyridine and 0.1 g of 4-(N,N-dimethylamino)-pyridine were added, followed by the dropwise addition, at 50° C., of 2.2 g (0.03 mol) of acetyl chloride dissolved in 20 ml of tetrahydrofuran. After a reaction time of 72 hours at 25° C., the mixture was evaporated down, the residue was taken up with methyl tert-butyl ether, the solution was washed with dilute $NaHCO_3$ solution and the organic phase was dried and evaporated down.

Yield 4.3 g (78% of theory), IR bands: 2958, 1769, 1492, 1366, 1204 $cm^{-3}$

The following compounds can be prepared in a similar manner.

TABLE 1

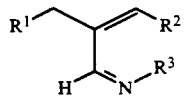

| No. | $R^1$ | $R^2$ | $R^3$ | m.p. (°C.)/IR $(cm^{-1})$/(NMR) |
|---|---|---|---|---|
| 1 | $n\text{-}C_3H_7$ | phenyl | OH | |
| 2 | $n\text{-}C_3H_7$ | 4-Cl—Ph | OH | |
| 3 | $n\text{-}C_3H_7$ | 4-F—Ph | OH | 91–93 |
| 4 | $n\text{-}C_3H_7$ | 4-F—Ph | $NH\text{—}CONH_2$ | 152 |
| 5 | $n\text{-}C_3H_7$ | 4-Me—Ph | OH | |
| 6 | $n\text{-}C_3H_7$ | 2-Cl—Ph | OH | |
| 7 | $n\text{-}C_3H_7$ | 2-F—Ph | OH | |
| 8 | $n\text{-}C_3H_7$ | 2,4-$Cl_2$Ph | OH | |
| 9 | $n\text{-}C_3H_7$ | 3-pyridine | OH | 118–121 |
| 10 | $n\text{-}C_3H_7$ | 3-pyridine | OMe | |
| 11 | $n\text{-}C_3H_7$ | 3-pyridine | OEt | |
| 12 | $n\text{-}C_3H_7$ | 3-pyridine | O—CO—Me | 0.9–2.6(9, m); 2.2(3, s); 6.8–8.7(6, m) |
| 13 | $n\text{-}C_3H_7$ | 3-pyridine | O—CO—Ph | 0.9–2.7(9, m); 6.8–8.7(11, m) |
| 14 | $n\text{-}C_3H_7$ | 4-pyridine | OH | |
| 15 | $n\text{-}C_3H_7$ | 2-pyridine | OH | |
| 16 | $n\text{-}C_3H_7$ | 1-naphthyl | OH | |
| 17 | $n\text{-}C_3H_7$ | 2-naphthyl | OH | |
| 18 | $n\text{-}C_3H_7$ | 4-biphenyl | OH | |
| 19 | n-Bu | phenyl | OH | |
| 20 | n-Bu | 4-Cl—Ph | OH | |
| 21 | n-Bu | 4-F—Ph | OH | |
| 22 | n-Bu | 4-Me—Ph | OH | |
| 23 | n-Bu | 2-Cl—Ph | OH | |
| 24 | n-Bu | 2-F—Ph | OH | |
| 25 | n-Bu | 2,4-$Cl_2$—Ph | OH | |
| 26 | n-Bu | 3-pyridine | OH | |
| 27 | t-Bu | Ph | OH | |
| 28 | t-Bu | 4-Cl—Ph | OH | 108–110 |
| 29 | t-Bu | 4-Cl—Ph | OMe | |
| 30 | t-Bu | 4-Cl—Ph | OEt | 2959, 1490, 1092, 1055 |
| 31 | t-Bu | 4-Cl—Ph | O—CO—Me | 2961, 1769, 1490, 1203 |
| 32 | t-Bu | 4-Cl—Ph | O—CO—Ph | |
| 33 | t-Bu | 4-Cl—Ph | NH—Ph | |
| 34 | t-Bu | 4-F—Ph | OH | |
| 35 | t-Bu | 4-F—Ph | O—CO—Me | |
| 36 | t-Bu | 4-Me—Ph | OH | |
| 37 | t-Bu | 2-Cl—Ph | OH | |
| 38 | t-Bu | 2-F—Ph | OH | |
| 39 | t-Bu | 2,4-$Cl_2$—Ph | OH | |
| 40 | t-Bu | 3-pyridine | OH | 178 |
| 41 | t-Bu | 3-pyridine | O—CO—Me | 0.8–2.7(14, m); 6.9–8.7(6, m) |
| 42 | t-Bu | cyclohexyl | OH | 88 |
| 43 | t-Bu | cyclohexyl | OMe | 2930, 2852, 1448, 1059 |
| 44 | t-Bu | cyclohexyl | OEt | 2929, 2852, 1448, 1056 |
| 45 | t-Bu | cyclohexyl | O—CO—Me | 2930, 2853, 1773, 1366, 1202 |
| 46 | t-Bu | cyclohexyl | O—CO—Ph | <50 |
| 47 | t-Bu | cyclohexyl | NH—Ph | 123 |
| 48 | t-Bu | cyclohexyl | 4-Br—Ph | 2928, 2852, 1612, 1481, 825 |
| 49 | n-pentyl | Ph | OH | |

TABLE 1-continued

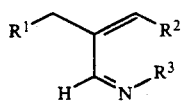

| No. | R¹ | R² | R³ | m.p. (°C.)/IR (cm⁻¹)/(NMR) |
|---|---|---|---|---|
| 50 | n-pentyl | 4-Cl—Ph | OH | |
| 51 | n-pentyl | 4-F—Ph | OH | |
| 52 | n-pentyl | 4-Me—Ph | OH | |
| 53 | n-pentyl | 2-Cl—Ph | OH | |
| 54 | n-pentyl | 2-F—Ph | OH | |
| 55 | n-pentyl | 2,4-Cl₂—PH | OH | |
| 56 | n-pentyl | 3-pyridine | OH | 120 |
| 57 | n-pentyl | 3-pyridine | OMe | 0.9–3.9(16, m); 6.5–8.6(6, m) |
| 58 | n-pentyl | 3-pyridine | OEt | 0.9–4.2(18, m); 6.5–8.6(6, m) |
| 59 | n-pentyl | 3-pyridine | O—CO—Me | 0.9–2.6(16, m); 6.4–8.7(6, m) |
| 60 | n-pentyl | 3-pyridine | O—CO—Ph | 0.9–2.8(13, m); 6.7–8.7(11, m) |
| 61 | n-pentyl | 3-pyridine | NH—Ph | 0.9–2.7(13, m); 6.4–8.6(11, m) |
| 62 | CH₂⊕ | Ph | OH | |
| 63 | CH₂⊕ | 4-Cl—Ph | OH | |
| 64 | CH₂⊕ | 4-F—Ph | OH | |
| 65 | CH₂⊕ | 4-Me—Ph | OH | |
| 66 | CH₂⊕ | 2-Cl—Ph | OH | |
| 67 | CH₂⊕ | 2-F—Ph | OH | |
| 68 | CH₂⊕ | 2,4-Cl₂—Ph | OH | |
| 69 | CH₂⊕ | 3-pyridine | OH | |
| 70 | n-Hexyl | Ph | OH | |
| 71 | n-Hexyl | 4-Cl—Ph | OH | |
| 72 | n-Hexyl | 4-F—Ph | OH | |
| 73 | n-hexyl | 4-Me—Ph | OH | |
| 74 | n-hexyl | 2-Cl—Ph | OH | |
| 75 | n-hexyl | 2-F—Ph | OH | |
| 76 | n-hexyl | 2,4-Cl₂—Ph | OH | |
| 77 | n-hexyl | 3-pyridine | OH | |
| 78 | CH₂—CH₂⊕ | Ph | OH | |
| 79 | CH₂—CH₂⊕ | 4-Cl—Ph | OH | |
| 80 | CH₂—CH₂⊕ | 4-F—Ph | OH | |
| 81 | CH₂—CH₂⊕ | 4-Me—Ph | OH | |
| 82 | CH₂—CH₂⊕ | 2-Cl—Ph | OH | |
| 83 | CH₂—CH₂⊕ | 2-F—Ph | OH | |
| 84 | CH₂—CH₂⊕ | 2,4-Cl₂—Ph | OH | |
| 85 | CH₂—CH₂⊕ | 3-pyridine | OH | |
| 86 | Ph | Ph | OH | |
| 87 | Ph | 4-Cl—Ph | OH | |
| 88 | Ph | 4-F—Ph | OH | |
| 89 | Ph | 4-Me—Ph | OH | |
| 90 | Ph | 2-Cl—Ph | OH | |

TABLE 1-continued

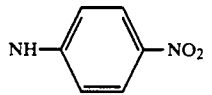

| No. | R¹ | R² | R³ | m.p. (°C.)/IR (cm⁻¹)/(NMR) |
|---|---|---|---|---|
| 91 | Ph | 2-F—Ph | OH | |
| 92 | Ph | 2,4-Cl₂—Ph | OH | |
| 93 | Ph | 3-pyridine | OH | |
| 94 | Ph | n-Bu | OH | |
| 95 | Ph | t-Bu | OH | |
| 96 | Ph | n-pentyl | OH | |
| 97 | Ph | CH₂─⟨⟩ | OH | |
| 98 | Ph | CH₂─⟨⟩ | OMe | |
| 99 | Ph | CH₂─⟨⟩ | OEt | |
| 100 | Ph | CH₂─⟨⟩ | O—CO—Me | |
| 101 | Ph | CH₂─⟨⟩ | O—CO—Ph | |
| 102 | Ph | CH₂─⟨⟩ | NH—Ph | |
| 103 | Ph | CH₂─⟨⟩ | NH—C₆H₄—NO₂ | |
| 104 | 4-Cl—Ph | CH₂─⟨⟩ | NH—CO—NH₂ | 0.9–4.1(13, m); 6.0–7.5(6, m) |
| 105 | Ph | n-hexyl | OH | |
| 106 | Ph | CH₂—CH₂─⟨⟩ | OH | |
| 107 | Ph | CH₂—CH₂─⟨⟩ | OMe | |
| 108 | Ph | CH₂—CH₂─⟨⟩ | OEt | 2956, 2867, 1052, 698 |
| 109 | Ph | CH₂—CH₂─⟨⟩ | O—CO—Me | 2956, 2866, 1770, 1366, 1204 |
| 110 | Ph | CH₂—CH₂─⟨⟩ | O—CO—Ph | 2956, 2907, 1749, 1257, 1245 |
| 111 | Ph | CH₂—CH₂─⟨⟩ | NH—Ph | 2955, 2904, 2865, 1600, 1495 |
| 112 | Ph | CH₂—CH₂ | NH—C₆H₃(NO₂)₂ | 145–148 |
| 113 | Ph | CH₂—CH₂─⟨⟩ | NH—CO—CH₂ | 2955, 2907, 1692, 1582, 698 |
| 114 | Ph | CH₂—CH₂—Ph | OH | 3026, 2925, 1495, 1452, 698 |
| 115 | Ph | CH₂—CH₂—Ph | OMe | 2935, 1495, 1452, 1047, 698 |
| 116 | Ph | CH₂—CH₂—Ph | OEt | 2931, 1495, 1453, 1051, 698 |
| 117 | Ph | CH₂—CH₂—Ph | O—CO—Me | 3026, 1766, 1453, 1204, 700 |
| 118 | Ph | CH₂—CH₂—Ph | O—CO—Ph | 1746, 1451, 1257, 1246, 700 |
| 119 | Ph | CH₂—CH₂—Ph | NH—Ph | 3025, 1602, 1494, 1258, 697 |

TABLE 1-continued $$\begin{array}{c} R^1\diagdown\!\!\!\!\diagup\!\!\!\!R^2 \\ H\diagdown\!\!\!\!\diagup N\diagdown R^3 \end{array}$$

| No. | R¹ | R² | R³ | m.p. (°C.)/IR (cm⁻¹)/(NMR) |
|---|---|---|---|---|
| 120 | Ph | CH₂—CH₂—Ph | NH—(2,4-dinitrophenyl) | 144–146 |
| 121 | Ph | CH₂—CH₂—Ph | NH—CO—NH₂ | 3463, 1693, 1582, 696 |
| 122 | 4-Cl—Ph | Ph | OH | |
| 123 | 4-Cl—Ph | 4-Cl—Ph | OH | |
| 124 | 4-Cl—Ph | 4-F—Ph | OH | 152–154 |
| 125 | 4-Cl—Ph | 4-F—Ph | OCH₃ | 3.7–3.9(5, m); 6.8–7.9(10, m) |
| 126 | 4-Cl—Ph | 4-F—Ph | OEt | 1.1–4.2(7, m); 6.7–7.9(10, m) |
| 127 | 4-Cl—Ph | 4-F—Ph | O—CO—Me | 2.2–4.0(5, m); 7.0–8.2(10, m) |
| 128 | 4-Cl—Ph | 4-F—Ph | O—CO—Ph | 88 |
| 129 | 4-Cl—Ph | 4-F—Ph | NH—Ph | 142–144 |
| 130 | 4-Cl—Ph | 4-F—Ph | NH—(4-nitrophenyl) | 195–197 |
| 131 | 4-Cl—Ph | 4-F—Ph | NH—CO—CH₂ | 163–164 |
| 132 | 4-Cl—Ph | 4-Me—Ph | OH | |
| 133 | 4-Cl—Ph | 2-Cl—Ph | OH | |
| 134 | 4-Cl—Ph | 2-F—Ph | OH | |
| 135 | 4-Cl—Ph | 2,4-Cl₂—Ph | OH | |
| 136 | 4-Cl—Ph | CH₂-cyclohexyl | OH | 78 |
| 137 | 4-Cl—Ph | CH₂-cyclohexyl | OMe | 2958, 2900, 1492, 1052, 797 |
| 138 | 4-Cl—Ph | CH₂-cyclohexyl | OEt | 0.9–4.1(16, m); 3.7(2, s); 5.9–7.8(6, m) |
| 139 | 4-Cl—Ph | CH₂-cyclohexyl | O—CO—Me | 2958, 1769, 1492, 1366, 1204 |
| 140 | 4-Cl—Ph | CH₂-cyclohexyl | O—CO—Ph | 2958, 1748, 1491, 1244, 707 |
| 141 | 4-Cl—Ph | CH₂-cyclohexyl | NH—Ph | 0.9–3.8(13, m); 5.8–7.4(11, m) |
| 142 | 4-Cl—Ph | CH₂ | NH—(2,4-dinitrophenyl) | 154 |
| 143 | 4-Cl—Ph | CH₂ | NH—CO—NH₂ | 118 |
| 144 | 4-Cl—Ph | CH₂-cyclohexyl | O—CO—OEt | |
| 145 | 4-Cl—Ph | CH₂—CH₂-cyclohexyl | OH | |
| 146 | 4-Cl—Ph | CH₂—CH₂-cyclohexyl | OMe | |
| 147 | 4-Cl—Ph | CH₂—CH₂-cyclohexyl | OEt | |
| 148 | 4-Cl—Ph | CH₂—CH₂-cyclohexyl | O—CO—Me | |
| 149 | 4-Cl—Ph | CH₂—CH₂-cyclohexyl | O—CO—Ph | |

TABLE 1-continued
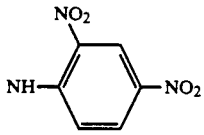
| No. | R¹ | R² | R³ | m.p. (°C.)/IR (cm⁻¹)/(NMR) |
|---|---|---|---|---|
| 150 | 4-Cl—Ph | CH₂—CH₂+ | NH—Ph | |
| 151 | 4-Cl—Ph | CH₂—CH₂+ | 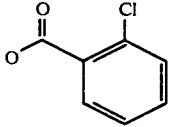 | |
| 152 | 4-Cl—Ph | CH₂—CH₂+ | NH—CO—NH₂ | |
| 153 | 4-F—Ph | Ph | OH | |
| 154 | 4-F—Ph | 4-Cl—Ph | OH | |
| 155 | 4-F—Ph | 4-F—Ph | OH | |
| 156 | 4-F—Ph | 4-Me—Ph | OH | |
| 157 | 4-F—Ph | 2-Cl—Ph | OH | 3280, 1506, 1432, 1219 |
| 158 | 4-F—Ph | 2-Cl—Ph | OCH₃ | 1508, 1218, 977, 761, 532 |
| 159 | 4-F—Ph | 2-Cl—Ph | OEt | |
| 160 | 4-F—Ph | 2-Cl—Ph | O—CO—Me | 2.1–3.9(5, m); 6.9–8.2(10, m) |
| 161 | 4-F—Ph | 2-Cl—Ph | O—CO—Ph | 1691, 1510, 1213, 710 |
| 162 | 4-F—Ph | 2-Cl—Ph | 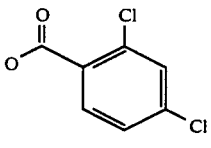 | 1508, 1235, 1036, 749 |
| 163 | 4-F—Ph | 2-Cl—Ph | 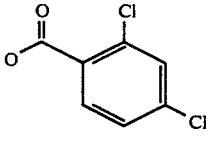 | |
| 164 | 4-F—Ph | 2-Cl—Ph | 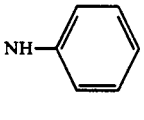 | 1508, 1232, 1037, 758 |
| 165 | 4-F—Ph | 2-Cl—Ph | 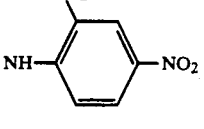 | 1603, 1507, 1258, 751 |
| 166 | 4-F—Ph | 2-Cl—Ph | 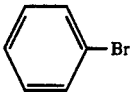 | 188 |
| 167 | 4-F—Ph | 2-Cl—Ph | phenyl | |
| 168 | 4-F—Ph | 2-Cl—Ph |  | 78 |
| 169 | 4-F—Ph | 2-Cl—Ph | NH—CO—NH₂ | |
| 170 | 4-F—Ph | 2-Cl—Ph | O—CH₂—Ph | |
| 171 | 4-F—Ph | 2-Cl—Ph | O—CO—OEt | |
| 172 | 4-F—Ph | 2-F—Ph | OH | |
| 173 | 4-F—Ph | 2-F—Ph | OH | |

TABLE 1-continued $$\begin{array}{c} R^1\diagdown\quad\diagup R^2\\ \diagup\diagdown\diagdown\\ H\quad N\diagdown R^3 \end{array}$$

| No. | R¹ | R² | R³ | m.p. (°C.)/IR (cm⁻¹)/(NMR) |
|-----|-----|-----|-----|-----|
| 174 | 4-F—Ph | CH₂+ | OH | 0.9-3.7(13, m); 5.3-7.8(6, m) |
| 175 | 4-F—Ph | CH₂+ | OMe | 2958, 1508, 1224, 1051 |
| 176 | 4-F—Ph | CH₂+ | OEt | 2959, 1508, 1223, 1052 |
| 177 | 4-F—Ph | CH₂+ | O—CO—Me | 2958, 1769, 1509, 1222, 1204 |
| 178 | 4-F—Ph | CH₂+ | O—CO—Ph | 2957, 1748, 1509, 1245, 708 |
| 179 | 4-F—Ph | CH₂+ | NH—Ph | 70 |
| 180 | 4-F—Ph | CH₂+ | NH—C₆H₃(NO₂)₂ (2,4-dinitro) | 161 |
| 181 | 4-F—Ph | CH₂+ | NH—CO—NH₂ | 53 |
| 182 | 4-F—Ph | CH₂+ | phenyl | |
| 183 | 4-F—Ph | CH₂+ | C₆H₄—Br | 2958, 1507, 1481, 1222 |
| 184 | 4-F—Ph | CH₂—CH₂+ | OH | |
| 185 | 4-F—Ph | CH₂—CH₂+ | OMe | |
| 186 | 4-F—Ph | CH₂—CH₂+ | OEt | |
| 187 | 4-F—Ph | CH₂—CH₂+ | O—CO—Me | |
| 188 | 4-F—Ph | CH₂—CH₂+ | O—CO—Ph | |
| 189 | 4-F—Ph | CH₂—CH₂+ | NH—Ph | |
| 190 | 4-F—Ph | CH₂—CH₂+ | NH—C₆H₃(NO₂)₂ (2,4-dinitro) | |
| 191 | 4-F—Ph | CH₂—CH₂+ | NH—CO—NH₂ | |
| 192 | 2-Cl—Ph | Ph | OH | |
| 193 | 2-Cl—Ph | 4-Cl—Ph | OH | |
| 194 | 2-Cl—Ph | 4-F—Ph | OH | |
| 195 | 2-Cl—Ph | 4-Me—Ph | OH | |
| 196 | 2-Cl—Ph | 2-Cl—Ph | OH | |
| 197 | 2-Cl—Ph | 2-F—Ph | OH | |
| 198 | 2-Cl—Ph | 2,4-Cl₂—Ph | OH | |
| 199 | 2-F—Ph | Ph | OH | |
| 200 | 2-F—Ph | 4-Cl—Ph | OH | |

TABLE 1-continued

Structure: R¹-CH₂-C(=CH-R²)-CH=N-R³

| No. | R¹ | R² | R³ | m.p. (°C.)/IR (cm⁻¹)/(NMR) |
|---|---|---|---|---|
| 201 | 2-F—Ph | 4-F—Ph | OH | |
| 202 | 2-F—Ph | 4-Me—Ph | OH | |
| 203 | 2-F—Ph | 2-Cl—Ph | OH | |
| 204 | 2-F—Ph | 2-F—Ph | OH | |
| 205 | 2-F—Ph | 2,4-Cl₂—Ph | OH | |

$$+ = -\underset{\underset{CH_3}{|}}{\overset{\overset{CH_3}{|}}{C}}-CH_3$$

TABLE 2

Structure: R¹-CH₂-C(=CH-R²)-CH=O

| No. | R¹ | R² |
|---|---|---|
| 1a | n-C₃H₇ | phenyl |
| 2a | n-C₃H₇ | 4-Cl—Ph |
| 3a | n-C₃H₇ | 4-F—Ph |
| 4a | n-C₃H₇ | 4-F—Ph |
| 5a | n-C₃H₇ | 4-Me—Ph |
| 6a | n-C₃H₇ | 2-Cl—Ph |
| 7a | n-C₃H₇ | 2-F—Ph |
| 8a | n-C₃H₇ | 2,4-Cl₂Ph |
| 9a | n-C₃H₇ | 3-pyridine |
| 10a | n-C₃H₇ | 3-pyridine |
| 11a | n-C₃H₇ | 3-pyridine |
| 12a | n-C₃H₇ | 3-pyridine |
| 13a | n-C₃H₇ | 3-pyridine |
| 14a | n-C₃H₇ | 4-pyridine |
| 15a | n-C₃H₇ | 2-pyridine |
| 16a | n-C₃H₇ | 1-naphthyl |
| 17a | n-C₃H₇ | 2-naphthyl |
| 18a | n-C₃H₇ | 4-biphenyl |
| 19a | n-Bu | phenyl |
| 20a | n-Bu | 4-Cl—Ph |
| 21a | n-Bu | 4-F—Ph |
| 22a | n-Bu | 4-Me—Ph |
| 23a | n-Bu | 2-Cl—Ph |
| 24a | n-Bu | 2-F—Ph |
| 25a | n-Bu | 2,4-Cl₂—Ph |
| 26a | n-Bu | 3-pyridine |
| 27a | t-Bu | Ph |
| 28a | t-Bu | 4-Cl—Ph |
| 29a | t-Bu | 4-Cl—Ph |
| 30a | t-Bu | 4-Cl—Ph |
| 31a | t-Bu | 4-Cl—Ph |
| 32a | t-Bu | 4-Cl—Ph |
| 33a | t-Bu | 4-Cl—Ph |
| 34a | t-Bu | 4-F—Ph |
| 35a | t-Bu | 4-F—Ph |
| 36a | t-Bu | 4-Me—Ph |
| 37a | t-Bu | 2-Cl—Ph |
| 38a | t-Bu | 2-F—Ph |
| 39a | t-Bu | 2,4-Cl₂—Ph |
| 40a | t-Bu | 3-pyridine |
| 41a | t-Bu | 3-pyridine |
| 42a | t-Bu | cyclohexyl |
| 43a | t-Bu | cyclohexyl |
| 44a | t-Bu | cyclohexyl |
| 45a | t-Bu | cyclohexyl |
| 46a | t-Bu | cyclohexyl |
| 47a | t-Bu | cyclohexyl |
| 48a | t-Bu | cyclohexyl |
| 49a | n-pentyl | Ph |
| 50a | n-pentyl | 4-Cl—Ph |
| 51a | n-pentyl | 4-F—Ph |
| 52a | n-pentyl | 4-Me—Ph |
| 53a | n-pentyl | 2-Cl—Ph |
| 54a | n-pentyl | 2-F—Ph |

TABLE 2-continued $$\underset{H}{\overset{R^1}{\underset{\parallel}{\bigvee}}}\underset{O}{\overset{}{\bigvee}}R^2$$

| No. | R¹ | R² | |
|---|---|---|---|
| 55a | n-pentyl | 2,4-Cl₂—PH | |
| 56a | n-pentyl | 3-pyridine | |
| 57a | n-pentyl | 3-pyridine | |
| 58a | n-pentyl | 3-pyridine | |
| 59a | n-pentyl | 3-pyridine | |
| 60a | n-pentyl | 3-pyridine | |
| 61a | n-pentyl | 3-pyridine | |
| 62a | CH₂— ⊥ | Ph | |
| 63a | CH₂— ⊥ | 4-Cl—Ph | bp 117–120° C./0.4 mbar |
| 64a | CH₂— ⊥ | 4-F—Ph | |
| 65a | CH₂— ⊥ | 4-Me—Ph | |
| 66a | CH₂— ⊥ | 2-Cl—Ph | |
| 67a | CH₂— ⊥ | 2-F—Ph | |
| 68a | CH₂— ⊥ | 2,4-Cl₂—Ph | |
| 69a | CH₂— ⊥ | 3-pyridine | |
| 70a | n-hexyl | Ph | |
| 71a | n-hexyl | 4-Cl—Ph | |
| 72a | n-hexyl | 4-F—Ph | |
| 73a | n-hexyl | 4-Me—Ph | |
| 74a | n-hexyl | 2-Cl—Ph | |
| 75a | n-hexyl | 2-F—Ph | |
| 76a | n-hexyl | 2,4-Cl₂—Ph | |
| 77a | n-hexyl | 3-pyridine | |
| 78a | CH₂—CH₂— ⊥ | Ph | |
| 79a | CH₂—CH₂— ⊥ | 4-Cl—Ph | |
| 80a | CH₂—CH₂— ⊥ | 4-F—Ph | |
| 81a | CH₂—CH₂— ⊥ | 4-Me—Ph | |
| 82a | CH₂—CH₂— ⊥ | 2-Cl—Ph | |
| 83a | CH₂—CH₂— ⊥ | 2-F—Ph | |
| 84a | CH₂—CH₂— ⊥ | 2,4-Cl₂—Ph | |
| 85a | CH₂—CH₂— ⊥ | 3-pyridine | |
| 86a | Ph | Ph | |
| 87a | Ph | 4-Cl—Ph | |
| 88a | Ph | 4-F—Ph | |
| 89a | Ph | 4-Me—Ph | |
| 90a | Ph | 2-Cl—Ph | |
| 91a | Ph | 2-F—Ph | |
| 92a | Ph | 2,4-Cl₂—Ph | |
| 93a | Ph | 3-pyridine | mp 94° C. |
| 94a | Ph | n-Bu | |
| 95a | Ph | t-Bu | |

TABLE 2-continued

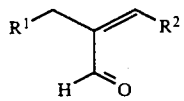

| No. | R¹ | R² |
|---|---|---|
| 96a | Ph | n-pentyl |
| 97a | Ph | CH₂+ |
| 98a | Ph | CH₂+ |
| 99a | Ph | CH₂+ |
| 100a | Ph | CH₂+ |
| 101a | Ph | CH₂+ |
| 102a | Ph | CH₂+ |
| 103a | Ph | CH₂+ |
| 104a | 4-Cl—Ph | CH₂+ |
| 105a | Ph | n-hexyl |
| 106a | Ph | CH₂—CH₂+ |
| 107a | Ph | CH₂—CH₂+ |
| 108a | Ph | CH₂—CH₂+ |
| 109a | Ph | CH₂—CH₂+ |
| 110a | Ph | CH₂—CH₂+ |
| 111a | Ph | CH₂—CH₂+ |
| 112a | Ph | CH₂—CH₂ |
| 113a | Ph | CH₂—CH₂+ |
| 114a | Ph | CH₂—CH₂—Ph |
| 115a | Ph | CH₂—CH₂—Ph |
| 116a | Ph | CH₂—CH₂—Ph |
| 117a | Ph | CH₂—CH₂—Ph |
| 118a | Ph | CH₂—CH₂—Ph |
| 119a | Ph | CH₂—CH₂—Ph |
| 120a | Ph | CH₂—CH₂—Ph |
| 121a | Ph | CH₂—CH₂—Ph |
| 122a | 4-Cl—Ph | Ph |
| 123a | 4-Cl—Ph | 4-Cl—Ph |
| 124a | 4-Cl—Ph | 4-F—Ph |
| 125a | 4-Cl—Ph | 4-F—Ph |
| 126a | 4-Cl—Ph | 4-F—Ph |
| 127a | 4-Cl—Ph | 4-F—Ph |
| 128a | 4-Cl—Ph | 4-F—Ph |
| 129a | 4-Cl—Ph | 4-F—Ph |
| 130a | 4-Cl—Ph | 4-F—Ph |
| 131a | 4-Cl—Ph | 4-F—Ph |
| 132a | 4-Cl—Ph | 4-Me—Ph |
| 133a | 4-Cl—Ph | 2-Cl—Ph |
| 134a | 4-Cl—Ph | 2-F—Ph |
| 135a | 4-Cl—Ph | 2,4-Cl₂—Ph |

TABLE 2-continued

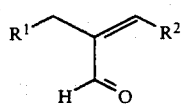

| No. | R¹ | R² | |
|---|---|---|---|
| 136a | 4-Cl—Ph | CH₂—⊲ | bp 119–122° C./0.01 mbar |
| 137a | 4-Cl—Ph | CH₂—⊲ | |
| 138a | 4-F—Ph | 2-Cl—Ph | bp 164–184° C./0.3 mbar |
| 139a | 4-Cl—Ph | 2,2-(CH₃)₂-n-propyl | bp 120° C./0.01 mbar |
| 140a | 4-F—Ph | 2,2-(CH₃)₂-n-propyl | bp 85° C./0.1 mbar |
| 141a | 4-Cl—Ph | —CH₂—CH₂—CH—(CH₃)₂—CH₃ | bp 120° C./0.1 mbar |
| 142a | 1,1-(CH₃)₂-n-ethyl | —CH₂—CH₂—CH—(CH₃)—CH₃ | bp 110–130° C./0.3 mbar |
| 143a | 1,1-(CH₃)₂-n-ethyl | 4-Cl—Ph | bp 120° C./0.4 mbar |
| 144a | 4-F—Ph | 3-pyridine | bp 155° C./0.1 mbar |
| 145a | 4-Cl—Ph | 4-F—Ph | mp 84–85.5° C. |
| 146a | 4-Cl—Ph | 2,4-dichloro-Ph | mp 130.5–131.5° C. |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals.
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosorium species in cereals,
*Septoria nodorum* in wheat.
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in vegetables and fruit.

The compounds are applied by spraying or dusting the plants with the active ingredients or treating the seeds of the plants with the active ingredients. They may be applied before or after infection of the plants or seeds by the fungi. Either the fungi themselves, or the plants, seeds, materials or soil to be protected against fungal attack are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner. for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g. crude oil fractions), alcohols (e.g., methanol, butanol), ketones (e.g., cyclohexanone), amines (e.g., ethanolamine, dimethylformamide), and water; carriers such as ground natural minerals (e.g. kaolins, aluminas, talc and chalk and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

The fungicidal agents generally contain from 0.1 to 95, and preferably from 0.5 to 90, wt. % of active ingredient. The application rates are from 0.02 to 3 kg or more of active ingredient per hectare, depending on the type of effect desired. The novel compounds may also be used for protecting materials (wood), for example against *Paecilomyces variotii*, When the active ingredients are used for treating seed, amounts of from 0.001 to 50, and preferably from 0.01 to 10, g per kg of seed are usually employed.

The agents and the ready-to-use formulations prepared from them, such as solutions, emulsions, suspensions, powders, dusts. Pastes and granules, are applied in conventional manner, for example by spraying, atomizing, dusting, scattering, dressing or watering.

Examples of formulations are given below.

I. 90 parts by weight of compound no. 109 (Table 1) is mixed with 10 parts by weight of N-methyl-α-pyrrolidone. A mixture is obtained which is suitable for application in the form of very fine drops.

II. 20 parts by weight of compound no. 136 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 139 is dissolved in a mixture consisting of 40 parts by weight of cyclohexanone, 30 parts by weight of isobutanol, 20 parts by weight of the adduct of 40 moles of ethylene oxide and mole of castor oil. By pouring the solution into water and finely distributing it therein, an aqueous dispersion is obtained.

IV. 20 parts by weight of compound no. 159 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and i mole of castor oil. By pouring the solution into water and uniformly distributing it therein, an aqueous dispersion is obtained.

V. 80 parts by weight of compound no. 168 is well mixed with 3 parts by weight of the sodium salt of diisobutylnaphthalene-α-sulfonic acid. 10 parts by weight of the sodium salt of a lignin-sulfonic acid obtained from a sulfite waste liquor and 7 parts by weight of powdered silica gel. and triturated in a hammer mill. By uniformly distributing the mixture in water, a spray liquor is obtained.

VI. 3 parts by weight of compound no. 174 is intimately mixed with 97 parts by weight of particulate kaolin. A dust is obtained containing 3% by weight of the active ingredient.

VII. 30 parts by weight of compound no. 109 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 136 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 139 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides growth regulators, and fungicides, and may furthermore be mixed and applied together with fertilizers. Admixture with other fungicides frequently results in an increase in the fungicidal spectrum.

Use example
Action on *Pyricularia oryzae* (protective)
Leaves of pot-grown rice seedlings of the "Bahia" variety were sprayed to runoff with aqueous emulsions containing (dry basis) 80% of active ingredients and 20% of emulsifier, and inoculated 24 hours later with an aqueous spore suspension of Pyricularia oryzae. The plants were then set up in climatic cabinets at from 22° to 24° C. and a relative humidity of 95 to 99%. The extent of fungus spread was determined after 6 days. The results show that active ingredients 109, 136, 139, 159, 168 and 174, applied as 0.05 wt. % spray liquors, have a good fungicidal action (90%).

We claim:
1. A compound of the formula I

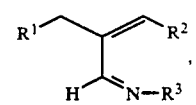

wherein $R^1$ and $R^2$ are each phenyl, biphenylyl, or naphthyl and these radicals may be mono- to tri-substituted by halogen, nitro, phenoxy, amino, haloalkyl, alkyl or alkoxy, each of 1 to 4 carbon atoms, or are each $C_1$–$C_8$-alkyl which is unsubstituted or substituted by phenyl, halophenyl or $C_1$–$C_4$-alkylphenyl, $R^3$ is a radical $OR^4$, where $R^4$ is hydrogen, $C_1$–$C_6$-halobenzoyl alkyl,

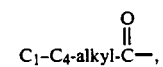

benzoyl or halobenzoyl or $R_3$ is a radical $NHR^5$, where $R^5$ is hydrogen, phenyl, nitrophenyl, or the carbamide group $CONH_2$.

2. Compounds of the formula I as set forth in claim 1, where $R^2$ is 2,2-dimethylpropyl, $R^3$ is OH, and $R^1$ is phenyl which is unsubstituted or substituted by one or two identical or different radicals selected from the group consisting of fluoro, chloro, bromo and methyl.

3. A fungicidal composition containing a carrier and a fungicidally effective amount of a 1-azabutadiene of the formula I

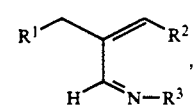

where $R^1$ and $R^2$ are each phenyl, biphenyly, or naphthyl and these radicals may be mono- to tri-substituted by halogen, nitro, phenoxy, amino, haloalkyl, alkyl or alkoxy, each of 1 to 4 carbon atoms, or are each $C_1$–$C_8$-alkyl which is unsubstituted or substituted by phenyl, halophenyl or $C_1$–$C_4$-alkylphenyl, $R^3$ is a radical $OR^4$, where $R^4$ is hydrogen, $C_1$–$C_6$-halobenzoyl, alkyl,

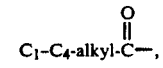

benzoyl or halobenzoyl or $R_3$ is a radical $NHR^5$, where $R^5$ is hydrogen, phenyl, nitrophenyl, or the carbamide group $CONH_2$.

4. A compound of the formula I as set forth in claim 1, where $R^1$ is phenyl, $R^2$ is 3,3-dimethylbutyl and $R^3$ is acetyloxy.

5. A compound of the formula I as set forth in claim 1, where $R^1$ is 4-chlorophenyl, $R^2$ is 2,2-dimethylpropyl and $R^3$ is OH.

6. A compound of the formula I as set forth in claim 1, where $R^1$ is 4-chlorophenyl, $R^2$ is 2,2-dimethylpropyl and $R^3$ is acetyloxy.

7. A compound of the formula I

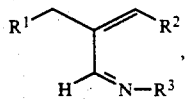

wherein $R^1$ is phenyl, biphenylyl, or naphthyl, and these radicals may be mono- to tri-substituted by halogen, nitro, phenoxy, amino, haloalkyl, alkyl or alkoxy, each of 1 to 4 carbon atoms, or is $C_1$–$C_8$-alkyl which is unsubstituted or substituted by phenyl, halophenyl or $C_1$–$C_4$-alkylphenyl; $R^2$ is biphenylyl which may be mono-to tri-substituted by halogen, nitro, phenoxy, amino, haloalkyl, alkyl or alkoxy, each of 1 to 4 carbon atoms, or is phenyl substituted by 1 to 3 groups selected from halogen, nitro, phenoxy, amino, haloalkyl, or alkoxy, each of 1 to 4 carbon atoms, or is naphthyl which may be mono- to tri-substituted by halogen, nitro, phenoxy, amino, haloalkyl, alkyl or alkoxy, each of 1 to 4 carbon atoms, or is $C_1$–$C_8$-alkly which is unsubstituted or substituted by phenyl, halophenyl or $C_1$–$C_4$-alkylphenyl; and $R^3$ is phenyl, halophenyl, or $C_1$–$C_4$-alkylphenyl.

8. A fungicidal composition containing a carrier and a fungicidally effective amount of a compound according to claim 7.

* * * * *